(12) United States Patent
Watson et al.

(10) Patent No.: US 7,741,473 B2
(45) Date of Patent: Jun. 22, 2010

(54) PROCESS FOR THE PREPARATION OF 4,6-DISUBSTITUTED-TETRAHYDRO-FURO, THIENO, PYRROLO AND CYCLOPENTA-[3,4][1,3]DIOXOLES

(75) Inventors: Paul S. Watson, Carrboro, NC (US); James G. Douglass, III, Apex, NC (US); Bob Suchozak, Newmarket (CA); Subramanian Pandiaraju, Brampton (CA); Craig E. Dixon, Whitby (CA); Daniel Levin, Toronto (CA)

(73) Assignee: Inspire Pharmaceuticals, Inc., Durham, NC (US)

( * ) Notice: Subject to any disclaimer, the term of this patent is extended or adjusted under 35 U.S.C. 154(b) by 1028 days.

(21) Appl. No.: 11/393,374

(22) Filed: Mar. 30, 2006

(65) Prior Publication Data

US 2006/0234976 A1 Oct. 19, 2006

Related U.S. Application Data

(60) Provisional application No. 60/666,788, filed on Mar. 30, 2005.

(51) Int. Cl.
*C07H 19/067* (2006.01)
*C07H 19/167* (2006.01)
(52) U.S. Cl. .................. 536/27.11; 536/27.62; 536/28.5
(58) Field of Classification Search ........................ None
See application file for complete search history.

(56) References Cited

U.S. PATENT DOCUMENTS

| | | | | |
|---|---|---|---|---|
| 6,867,199 B2 * | 3/2005 | Rideout et al. | ................ | 514/47 |
| 6,897,201 B2 * | 5/2005 | Boyer et al. | ................ | 514/51 |
| 7,018,985 B1 * | 3/2006 | Boyer et al. | ................ | 514/48 |
| 7,101,860 B2 * | 9/2006 | Boyer et al. | ................ | 514/43 |
| 7,115,585 B2 * | 10/2006 | Yerxa et al. | ................ | 514/48 |
| 7,132,408 B2 * | 11/2006 | Boyer et al. | ................ | 514/45 |
| 7,335,648 B2 * | 2/2008 | Plourde et al. | ................ | 514/46 |
| 7,368,438 B2 * | 5/2008 | Plourde et al. | ................ | 514/46 |
| 7,435,724 B2 * | 10/2008 | Douglass et al. | ................ | 514/45 |
| 7,452,870 B2 * | 11/2008 | Boyer et al. | ................ | 514/45 |
| 7,504,497 B2 * | 3/2009 | Douglass et al. | ................ | 536/27.3 |
| 2004/0220133 A1 | 11/2004 | Boyer et al. | | |
| 2007/0249556 A1 * | 10/2007 | Brubaker et al. | ................ | 514/47 |

FOREIGN PATENT DOCUMENTS

WO WO2005/040174 A1 * 5/2005
WO WO2007/140333 A2 * 12/2007

OTHER PUBLICATIONS

Douglas et al., "Adenosine Analogues as Inhibitors of P2Y12 Mediated Platelet Aggregation," Bioorganic & Medicinal Chemistry Letters, 18(6), 2167-2171 (2008).*
A. Hampton et al., *J. Am. Chem. Soc.*, 1965, 87(23), 5481.
D. Lipkin et al., *Tetrahedron Lett.*, 1959, 21, 18-21.
M. Smith et al., *J. Am. Chem. Soc.*, 1962, 84(3), 430-440.
H. Wakuda, Nippon Kagaku Kaishi, *Journal of the Chemical Society of Japan, Chemistry and Industrial Chemistry*, 1998, 1, 40.
International Search Report PCT/US2006/012626, mailed Aug. 11, 2006.
Wakuda, Haruhisa, et al., "Conformational Analysis of 2', 3'-O-alkylideneadenosines" Nippon Kagaku Kaishi, (1), 40-44 Coden: NKAKB8.
Bakthavachalam V, et al: "Synthesis Stereochemistry Intramolecular Cyclization and Rates of Hydrolysis of Adenosine 2' 3' Acetals", carbohydrate research, vol. 170, No. 1, 1987, pp. 124-136.

* cited by examiner

*Primary Examiner*—Lawrence E Crane
(74) *Attorney, Agent, or Firm*—Howrey LLP; Viola T. Kung

(57) ABSTRACT

The present invention is directed to a processes for the synthesis of trans isomer of 4,6-disubstituted-tetrahydro-furo, thieno, pyrrolo and cyclopenta-[3,4][1,3]dioxoles (Formula I). The process comprises the steps of: (a) obtaining a compound of Formula II, which is a mixture of cis and trans-diastereomers, and (b) chemically decomposing the compound of Formula II in a solution comprising a solvent and an acid that is a hydrogen donor or an electron pair acceptor, whereby the cis diastereomer is decomposed and the compound of Formula I is obtained. The compounds prepared by the present invention are useful in treating diseases or conditions associated with platelet aggregation and/or platelet activation.

19 Claims, No Drawings

US 7,741,473 B2

PROCESS FOR THE PREPARATION OF 4,6-DISUBSTITUTED-TETRAHYDRO-FURO, THIENO, PYRROLO AND CYCLOPENTA-[3,4][1,3]DIOXOLES

This application claims priority to U.S. provisional application No. 60/666,788, filed Mar. 30, 2005. The content of which is incorporated herein by reference in its entirety.

TECHNICAL FIELD

The present invention relates generally to the synthesis of the trans isomers of 4,6-disubstituted-tetrahydro-furo, thieno, pyrrolo and cyclopenta-[3,4][1,3]dioxoles such as 4-substituted -6-purinyl or pyrimidinyl tetrahydro-furo-[3,4][1,3]dioxoles and intermediates thereof. The compounds prepared by the present invention are useful in treating diseases or conditions associated with platelet aggregation and/or platelet activation.

BACKGROUND OF THE INVENTION

An active area of research is in the discovery of $P2Y_{12}$ antagonists. Different methods have been described for the synthesis of tetrahydro-furo[3,4][1,3]dioxole cores [D. Lipkin et al., Tetrahedron Lett., 1959, 21, 18-21; H. G. Korana et al., *J. Am. Chem. Soc.*, 1962, 84(3), 430-440.; A. Hamilton et al., *J. Am. Chem. Soc.*, 1965, 87(23), 5481; H. Wakuda, Nippon Kagaku Kaishi, *Journal of the Chemical Society of Japan, Chemistry and Industrial Chemistry*, 1998, 1, 40]. Although these methods appear to be general in scope, they do not adequately address the selective preparation of either cis or trans diastereomer, or to produce diastereomerically enriched products. In addition, these methods described in the literature are very time consuming (lasting over four days), and they sometimes involve the use of highly flammable solvents.

There is a need for a practical process for the preparation of a trans diastereomer of 4,6-disubstituted-tetrahydro-furo, thieno, pyrrolo and cyclopenta-[3,4][1,3]dioxoles.

SUMMARY OF THE INVENTION

The present invention is directed to processes for the synthesis of trans isomers of 4,6-disubstituted-tetrahydro-furo, thieno, pyrrolo and cyclopenta-[3,4][1,3]dioxoles (Formula I). The process comprises the steps of: (a) obtaining a compound of Formula II, which is a mixture of cis and trans-diastereomers,

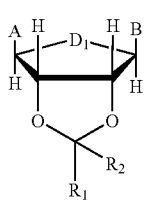

Formula II (b) chemically decomposing the compound of Formula II in a solution comprising a solvent and an acid that is either an electron pair acceptor or a proton donor, whereby the cis diastereomer is decomposed and the compound of Formula I is obtained.

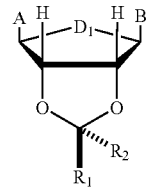

Formula I

The process of the present invention can be used to prepare a compound of general Formula I, which are useful in preventing or treating diseases or conditions associated with platelet aggregation and/or platelet activation; such diseases include venous thrombosis, thrombophlebitis, arterial embolism, coronary and cerebral arterial thrombosis, unstable angina, myocardial infarction, stroke, cerebral embolism, kidney embolisms and pulmonary embolisms.

DETAILED DESCRIPTION OF THE INVENTION

Definitions

When present, unless otherwise specified, the following terms are generally defined as, but are not limited to, the following:

Alkyl groups are from 1 to 12 carbon atoms inclusively, either straight chained or branched, are more preferably from 1 to 8 carbon atoms inclusively, and most preferably 1 to 6 carbon atoms inclusively.

Alkylene chains are from 2 to 20 carbon atoms inclusively, have two points of attachment to the to the molecule to which they belong, are either straight chained or branched, can contain one or more double and/or triple bonds, are more preferably from 4 to 18 atoms inclusively, and are most preferably from 6 to 14 atoms inclusively.

Alkenyl groups are from 1 to 12 carbon atoms inclusively, either straight or branched containing at least one double bond but can contain more than one double bond.

Alkynyl groups are from 1 to 12 carbon atoms inclusively, either straight or branched containing at least one triple bond but can contain more than one triple bond, and additionally can contain one or more double bonded moieties.

"Alkoxy" refers to the group alkyl-O— wherein the alkyl group is as defined above including optionally substituted alkyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl- groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl- groups preferably having from 1 to 6 carbon atoms in the alkenyl moiety and from 6 to 10 carbon atoms inclusively in the aryl moiety.

"Arylalkynyl" refers to aryl-alkynyl- groups preferably having from 1 to 6 carbon atoms inclusively in the alkynyl moiety and from 6 to 10 carbon atoms inclusively in the aryl moiety.

"Aryloxy" refers to the group aryl-O— wherein the aryl group is as defined above including optionally substituted aryl groups as also defined above.

"Cycloalkyl" refers to cyclic alkyl groups of from 3 to 12 carbon atoms inclusively having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 12 carbon atoms inclusively having a single cyclic ring or multiple condensed rings and at least one point of internal unsaturation, which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Cycloalkylalkyl" refers to cycloalkyl-alkyl- groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Heteroaryl" refers to a monovalent aromatic carbocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl-alkyl- groups preferably having from 1 to 6 carbon atoms inclusively in the alkyl moiety and from 6 to 10 carbon atoms inclusively in the heteroaryl moiety. Such arylalkyl groups are exemplified by pyridylmethyl and the like.

"Heteroarylalkenyl" refers to heteroaryl-alkenyl- groups preferably having from 1 to 6 carbon atoms inclusively in the alkenyl moiety and from 6 to 10 carbon atoms inclusively in the heteroaryl moiety.

"Heteroarylalkynyl" refers to heteroaryl-alkynyl- groups preferably having from 1 to 6 carbon atoms inclusively in the alkynyl moiety and from 6 to 10 carbon atoms inclusively in the heteroaryl moiety.

"Heterocyclyl" refers to a saturated or unsaturated group having a single ring or multiple condensed rings, from 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Preferred heterocyclyls include piperidinyl, pyrrolidinyl and tetrahydrofuryl.

Examples of heterocyclyls and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Positions occupied by hydrogen in the foregoing groups can be further substituted with substituents exemplified by, but not limited to, hydroxy, oxo, nitro, methoxy, ethoxy, alkoxy, substituted alkoxy, fluoro, chloro, bromo, iodo, methyl, ethyl, propyl, butyl, alkyl, substituted alkyl, thio, thioalkyl, acyl, carboxyl, alkoxycarbonyl, carboxamido, substituted carboxamido, alkylsulfonyl, alkylsulfinyl, alkylsulfonylamino, sulfonamido, substituted sulfonamide, cyano, amino, substituted amino, acylamino, trifluoromethyl, trifluoromethoxy, phenyl, aryl, substituted aryl, pyridyl, imidazolyl, heteroaryl, substituted heteroaryl, cyclopropyl, cyclobutyl, cyclopentyl, cyclohexyl, cycloalkyl, substituted cycloalkyl, pyrrolidinyl, piperidinyl, morpholino, and heterocycle; and preferred heteroatoms are oxygen, nitrogen, and sulfur. It is understood that where open valences exist on these substituents they can be further substituted with alkyl, cycloalkyl, aryl, heteroaryl, and/or heterocycle groups, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

Chemical decomposition refers to the degradation of a molecule into its constituents by a chemical reaction, specifically the decomposition of the acetal or ketal functionality that is formed between the 2' and 3' alcohol groups on the tetrahydro furan, thiophene, pyrrolidine or cyclopentane rings. This phrase is directed towards the selective hydrolysis of the less stable cis-diastereomer.

Diastereomers are stereoisomers (isomers of identical constitution but differing three-dimensional architecture), which do not bear a mirror-image relation to each other.

Metal counterion refers to a positively charged ion or complex, which serves as a pairing partner for the negative charge of the nucleophile. Examples of suitable metal counter ions include, but are not limited to positively charged ions or complexes of lithium, sodium, potassium; copper and any salts thereof, such as chloride, bromide or iodide; magnesium and any salts thereof, such as chloride, bromide or iodide; zinc and any salts thereof, such as chloride or bromide; cerium and any salts thereof, such as chloride or bromide; and calcium and any salts thereof, such as chloride or bromide. Examples of positively charged ions or complexes include $Li^+$, $Na^+$, $K^+$, $MgCl^+$, $MgBr^+$, $MgI^+$, $ZnCl^+$, $ZnBr^+$, $CaCl^+$, $CaBr^+$, $CuBr^+$, and $CuCl^+$.

Pharmaceutically acceptable salts are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$). In the case of mono- or di-phosphates of nucleosides of the present invention, the salt forms are typically to be alkali-earth metals such as sodium, potassium, lithium or basic salts such as ammonium. Pharmaceutically acceptable salts are generally prepared by reacting the free base or acid with stoichiometric amounts or with an excess of the desired salt-forming inorganic or organic acid or base in a suitable solvent or various combinations of solvents.

Solvates are addition complexes in which a compound is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toulene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definition of the compound of the present invention encompasses all possible hydrates and solvates, in any proportion, which possess the stated activity.

A stable compound is meant to indicate a compound that is sufficiently robust to survive isolation to a useful degree of purity from a reaction mixture, and formulation into an efficacious therapeutic agent.

Tautomers are compounds that can exist in one or more forms, called tautomeric forms, which can interconvert by way of a migration of one or more hydrogen atoms in the compound accompanied by a rearrangement in the position of adjacent double bonds. These tautomeric forms are in equilibrium with each other, and the position of this equilibrium will depend on the exact nature of the physical state of the compound. It is understood that where tautomeric forms are possible, the current invention relates to all possible tautomeric forms.

The inventors have unexpectedly discovered a reactivity difference between two diastereomeric species, differing at one asymmetric center, which makes the cis-isomer more susceptible to chemical decomposition. Based on the reactivity difference of the trans and cis isomers, the inventors have discovered a process for preparing a compound of Formula I, or a pharmaceutically acceptable salt, tautomer, solvate, or hydrate thereof:

Formula I

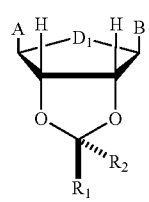

The process comprises the steps of:

(a) obtaining a compound of Formula II, which is a mixture of cis and trans-diastereomers; (cis and trans refer to the positions of hydrogens on the dioxole ring)

Formula II

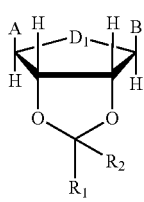

(b) chemically decomposing the compound of Formula II in a solution comprising an organic solvent and an acid that is either an electron pair acceptor or a proton, whereby the cis diastereomer is decomposed and the compound of Formula I is obtained;

wherein $D_1$ is $CH_2$, $NR_3$, O, or S;

$R_1$, $R_2$ and $R_3$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, aralkyl, substituted aralkyl, heterocycle and substituted heterocycle, with the proviso that $R_1$ and $R_2$ are not both hydrogen;

A is

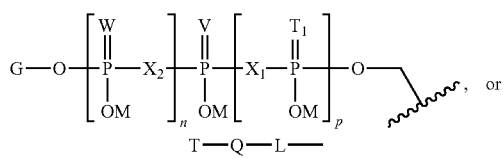

wherein;

n and p are 0, 1, or 2 such that the sum of n+p is from 0 to 3;

each M is independently hydrogen, $NH_4^+$, $Na^+$ or other pharmaceutically acceptable inorganic or organic counterions (such as metal counterions);

$T_1$, V and W are each independently selected from O or S;

$X_1$ and $X_2$ are independently O, NH, $CH_2$, CHF, CHCl, $CF_2$ or $CCl_2$;

G is M, or

G is

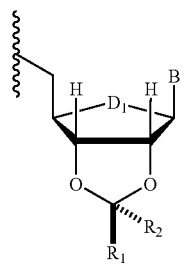

wherein:

L, Q and T are each independently $R_1$, (CO), O, S, $NHR_1$, $NR_1R_3$, $[NR_1(CO)]$, $N[(CO)R_1]$, with the proviso that a stable compound or structure is created by the selection; or Q and T is absent; or T is a heterocycle or substituted heterocycle;

each B is independently —$NHR_3$, alkyl, cycloalkyl, alkenyl, substituted alkenyl, alkynyl, substituted alkynyl, aralkyl, substituted aralkyl, aryl, substituted aryl, heterocycle and substituted heterocycle; or each B is independently a purine residue linked through the 9-position, as in Formula III:

Formula III

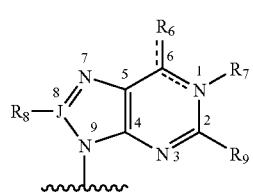

or a pyrimidine residue linked through the 1-position, as in Formula IV:

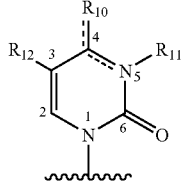

Formula IV wherein:
$R_6$ and $R_{10}$ are hydroxy, oxo, amino, mercapto, alkylthio, alkyloxy, aryloxy, alkylamino, cycloalkylamino, aralkylamino, arylamino, diaralkylamino, diarylamino, or dialkylamino, where the alkyl groups are optionally linked to form a heterocycle; or $R_6$ and $R_{10}$ are independently acylamino, acyl(alkyl)amino, acyl(alkenyl)amino, acyl(alkynyl)amino acyl(cycloalkyl)amino, acyl(aryl)amino, acyl(aralkyl)amino, acyl(heteroaryl)amino, or acyl(heteroarylalkyl(amino); or $R_6$ and $R_{10}$ are di-acylamino, with the acylamino moieties optionally linked to form a heterocycle; or when $R_6$ in a purine or $R_{10}$ in a pyrimidine has as its first atom nitrogen, $R_6$ and $R_7$ or $R_{10}$ and $R_{11}$ are taken together to form a 5-membered fused imidazole ring, optionally substituted on the etheno ring with hydrogen, alkyl, cycloalkyl, acyl, substituted acyl, aryl, substituted aryl, aralkyl or substituted aralkyl;

J is carbon or nitrogen, with the provision that when nitrogen, $R_8$ is not present;

$R_7$ is hydrogen, or is absent;

$R_8$ is hydrogen, alkyl, bromo, azido, alkylamino, arylamino, aralkylamino, alkoxy, aryloxy, aralkyloxy, alkylthio, arylthio, aralkylthio, or $R_{14}(C_{1-6}\text{-alkyl})R_{13}$—; where $R_9$ is hydrogen, chlorine, amino, monosubstituted amino, disubstituted amino, alkylthio, arylthio, or aralkylthio;

$R_{11}$ is hydrogen or acyl;

$R_{12}$ is hydrogen, alkyl, cycloalkyl, halo, alkenyl, substituted alkenyl, alkynyl, substituted alkynyl, aryl, substituted aryl, aralkyl or substituted aralkyl;

$R_{13}$ is amino, mercapto, oxo, or carbonyl; and $R_{14}$ is amino, mercapto, hydroxyl, or carboxyl.

The present invention is suitable for preparing Formula I compounds in a multigram scale, kilogram scale, multikilogram scale, or industrial scale, which is a scale sufficient to supply product for either clinical tests or distribution to consumers.

Preparation of Compound of Formula II

The compound of Formula II in step (a) can be prepared by any method known to a skilled person. In one embodiment, Formula II is prepared by reacting a compound of Formula VI with a compound of formula VII in the presence of an organic acid,

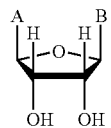

Formula VI

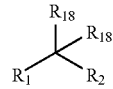

Formula VII wherein $R_{18}$ is independently O, alkoxy and hydroxyl; in the case when both $R_{18}$ are oxo, they are taken together to be a carbonyl group.

In preparing a compound of Formula II, a compound of Formula (VI) and a compound of Formula VII and a suitable solvent are added to a reaction vessel. The order of addition is determined by convenience, or by other process issues familiar to the artisan of process chemistry. While the reaction can be conducted in many solvents such as: dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide, propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, hexamethylphosphoramide, methylene chloride, tetrahydrofuran and 1,4-dioxane; methylene chloride, tetrahydrofuran and 1,4-dioxane are preferred when the use of a true solvent is necessary. In circumstances when the aldehyde, ketone or suitable derivative of Formula VII is a liquid, for example benzaldehyde and trans-cinnamaldehyde, this substance itself is the preferred solvent.

Conditions that can facilitate the reaction include the presence of an organic acid. Organic acids such as formic acid, acetic acid, methanesulfonic acid, trifluoro acetic acid, propionic acid, butyric acid, valeric acid, caproic acid, oxalic acid, benzenesulfonic acid, and p-toluenesulfonic acid are preferred; with trifluoroacetic acid being most preferred. The preferred amount of the organic acid to the starting formula (VI) is 6-12 equivalents. The preferred amount of aldehyde or ketone (Formula VII) to the starting formula (VI) is 6-12 equivalents. The reaction is preferably carried out between −10 to 25° C. The reaction is preferably monitored by HPLC, and is considered complete when the area of the mixture of diastereomers formed is <75% in relation to the starting formula (VI). Depending on the starting solvents and temperature, the reaction is generally done in 2-12 hours. The reaction can be quenched by the addition of an aqueous base solution. Examples of such base solutions include sodium, lithium, and potassium salts of carbonates; sodium, lithium, and potassium salts of bicarbonates; and sodium, lithium and potassium salts of hydroxides, with sodium hydroxide being preferred. Optionally, the reaction can be further quenched by diluting it with a co-solvent. Suitable co-solvents include, but are not limited to, acetonitrile (ACN), propionitrile, ethyl formate, methyl acetate, hexachloroacetone, acetone, ethyl methyl ketone, ethyl acetate, isopropyl acetate and t-butyl acetate; with ethyl acetate; isopropyl acetate and t-butyl acetate being preferred. The order of adding a co-solvent and an aqueous base solution can be varied; preferably, the co-solvent is added first. The aqueous and organic phases are preferably separated. The compounds of Formula II is isolated, preferably by filtration or centrifugation of the organic phase. This solid can be rinsed with the co-solvent. The product is preferably dried under vacuum preferably at a temperature in the range 30 to 60° C, to constant weight. The product is preferably dried under vacuum preferably at a temperature in the range 30 to 60° C., to constant weight.

Chemical Decomposition of a Compound of Formula II

A mixture of cis and trans isomers of a compound of formula (II), a suitable acid, and a suitable solvent system are added to a reaction vessel. The order of addition can be determined by convenience, or by other process issues familiar to the artisan of process chemistry.

Suitable acids for chemical decomposition include proton donors or electron pair acceptors (Lewis acids). Suitable proton donors are organic acids and inorganic acids whose $pK_a$ are about or less than 4.7. Suitable organic acids include formic acid, acetic acid, methanesulfonic acid, trifluoroacetic acid, propionic acid, butyric acid, valeric acid, caproic acid, oxalic acid, benzenesulfonic acid, and p-toluenesulfonic acid. P-toluenesulfonic acid is a preferred organic acid. The amount of the organic acid is typically based on the molar equivalents of the mixture of formula (II), and is in general 0.5-20, or 0.5-10 molar equivalents. As an example, 0.75-1.5 molar equivalents of p-toluenesulfonic acid can be used.

Suitable inorganic acids include hydrochloric acid, hydrobromic acid, hydroiodic acid, sulfuric acid, nitric acid, and phosphoric acid. The amount of the inorganic acid is typically based on the molar equivalents of the mixture of formula (II), and is in general 0.1-10, or 0.75-4 molar equivalents. As an example, 0.25-1 molar equivalents of hydrochloric acid can be used.

Suitable Lewis acids include boron trifluoride, boron trichloride, zinc chloride, iron trichloride, tin chloride, aluminum trichloride, and dimethyl bromoborane.

The reaction can be conducted in many solvent systems, which contain an organic solvent such as tetrahydrofuran, 1,3-dioxane, 1,4-dioxane, furan, ethylene glycol dimethyl ether, ethylene glycol diethyl ether, diethylene glycol dimethyl ether, diethylene glycol diethyl ether, triethylene glycol, anisole, methanol, ethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, dimethylformamide (DMF), dimethylacetamide (DMAC), 1,3-dimethyl-3,4,5,6-tetrahydro-2(1 H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide, propionitrile, acetone, N,N-dimethylpropionamide, and hexamethylphosphoramide. An aqueous tetrahydrofuran solvent system is preferred. The amount of water in the aqueous tetrahydrofuran solution is preferably 15 to 25%. In one embodiment, the chemical decomposition is carried out with p-toluenesulfonic acid in an aqueous tetrahydrofuran solvent system. In another embodiment, the chemical decomposition is carried out with hydrochloric acid in an acetonitrile solvent system.

The chemical decomposition is generally carried out between 20 to 100° C. For example, when the aldehyde component is trans-cinnamaldehyde (Formula VII), the reaction (decomposition) is done between 25 to 55° C. Additionally, when the aldehyde component is benzaldehyde (Formula VII), the reaction (decomposition) is done between 50 to 100° C. The reaction is preferably monitored by HPLC, and can be considered complete when the area ratio of the trans-diastereomer to the cis-diastereomer is >95:1, preferably >99:1. Depending on the starting solvents and temperature, the reaction is generally done in 2-24 hours.

The reaction can be quenched by the addition of an aqueous base solution. Examples of such base solutions include sodium, lithium, and potassium salts of carbonates; sodium, lithium, and potassium salts of bicarbonates; and sodium, lithium and potassium salts of hydroxides; sodium hydroxide being preferred. The aqueous and organic phases are preferably separated. The separation process is preferable performed between 20 to 70° C. Product crystallization can be facilitated by adding a co-solvent. Suitable co-solvents include, but are not limited to acetonitrile (ACN), propionitrile, ethyl formate, methyl acetate, hexachloroacetone, acetone, ethyl methyl ketone, ethyl acetate, isopropyl acetate, t-butyl acetate; with ethyl acetate, isopropyl acetate or t-butyl acetate being preferred. The compound of Formula I is isolated, preferably by filtration or centrifugation of the organic phase. The solid can be rinsed with the co-solvent. The product is preferably dried under vacuum at a temperature in the range 30 to 60° C., to a constant weight.

Depending on the specific compound or the specific acid chosen, the above chemical decomposition conditions can be varied and modified based on conditions that are known to cleave cyclic acetals, described on pages 201-230 of: Protective Groups in Organic Synthesis, $3^{rd}$ Ed., T. W. Greene and P. G. M. Wuts, John Wiley and Sons, Inc., New York, 1999.

Formula I Compounds

The process according to the present invention produces a compound of Formula I in various embodiments.

In one embodiment, Formula I is an acetal, wherein $R_1$ is alkyl, substituted alkyl, alkenyl, substituted alkenyl, alkynyl, substituted alkynyl, cycloalkyl, substituted cycloalkyl, aryl, substituted aryl, aralkyl, substituted aralkyl, heterocycle or substituted heterocycle, and $R_2$ is H. For example, $R_1$ is styryl and $R_2$ is H.

In another embodiment, each B of a Formula I compound is independently a purine residue linked through the 9-position, as in Formula III, or a pyrimidine residue linked through the 1-position, as in Formula IV; wherein $R_6$ and $R_{10}$ are independently acylamino, acyl(alkyl)amino, acyl(alkenyl) amino, acyl(alkynyl)amino acyl(cycloalkyl)amino, acyl(aryl)amino, acyl(aralkyl)amino, acyl(heteroaryl)amino, or acyl (heteroarylalkyl(amino); that falls within the scope of Formula V:

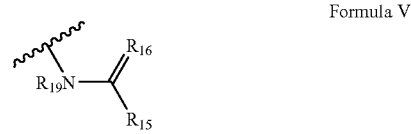

Formula V wherein:

$NR_{19}$ is the amino residue at the C-6 position in a purine or the amino residue at the C-4 position in a pyrimidine;

$R_{15}$ is amino, monosubstituted amino and disubstituted amino such that the moiety according to Formula V is a urea or thiourea;

when present, the substituents on $R_{15}$ are alkyl, cycloalkyl, alkenyl, substituted alkenyl, alkynyl, substituted alkynyl, aralkyl, substituted aralkyl, aryl, substituted aryl, heterocycle and substituted hetereocycle; or $R_{15}$ is alkoxy, aralkyloxy, aryloxy, substituted aralkyloxy, or substituted aryloxy, such that the moiety according to Formula V is a carbamate or thiocarbamate; or $R_{15}$ is hydrogen, alkyl, cycloalkyl, alkenyl, substituted alkenyl, alkynyl, substituted alkynyl, aralkyl, substituted aralkyl, aryl, substituted aryl, heterocycle and substituted heterocycle such that the moiety according to Formula V is an amide;

$R_{16}$ is oxygen, sulfur, or NCN (cyanoquanidine); and $R_{19}$ is H, alkyl, alkenyl, alkynyl, cycloalkyl, aryl, aralkyl, heteroaryl, or heteroarylalkyl; with H being preferred; or $R_6$ and $R_{10}$ are independently di-acylamino, falling under the definition of Formula Va:

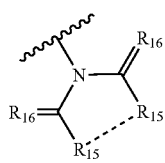

Formula Va where $R_{15}$ and $R_{16}$ are defined above, with the proviso that the two $R_{15}$ moieties may be optionally linked to form a heterocycle comprising 5 to 9 atoms In another embodiment, A of a Formula I compound is

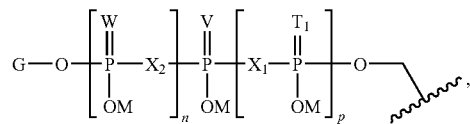

wherein n and p are 0, 1, or 2 such that the sum of n+P is from 0 to 3;

G is M;

W=V=$T_1$=O or S; and $X_1$ and $X_2$ are independently O, NH, $CH_2$, CHF, CHCl, $CF_2$ or $CCl_2$.

Preferably n=p=0, and W=V=$T_1$=$X_1$=$X_2$=O; such that A is a monophosphate.

In another embodiment, A of a Formula I compound is

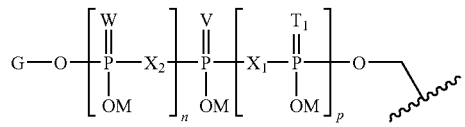

wherein n and p are 0, 1, or 2 such that the sum of n+p is from 0 to 3;

$T_1$, V and W are each independently selected from O or S;

$X_1$ and $X_2$ are independently O, NH, $CH_2$, CHF, CHCl, $CF_2$ or $CCl_2$;

G is

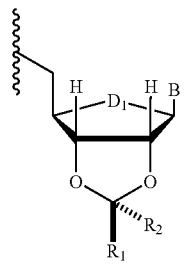

such that Formula I is a dinucleotide.

The process according to the present invention preferably produces a compound of formula I (a monophosphate adenosine urea), wherein:

$R_1$ is alkyl, substituted alkyl, alkenyl, substituted alkenyl, alkynyl, substituted alkynyl, cycloalkyl, substituted cycloalkyl, aryl, substituted aryl, aralkyl, substituted aralkyl, heterocycle and substituted heterocycle;

$R_2$=H;

$D_1$ is O;

A is

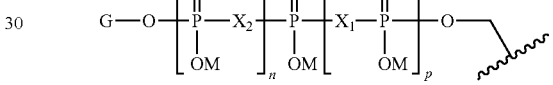

wherein;

n and p are 0;

each M is independently selected from the group consisting of hydrogen, $NH_4^+$, $Na^+$ or other pharmaceutically acceptable inorganic or organic counterions;

V is O;

G is M;

B is a purine residue linked through the 9-position, as in Formula III:

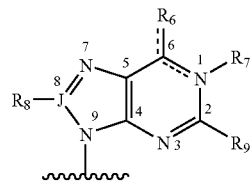

Formula III $R_6$ is acylamino and falls within the scope of Formula V:

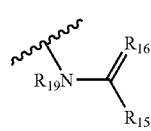

Formula V wherein:

J is carbon;

$R_7$ is absent;

$R_8$ and $R_9$ are hydrogen;

R$_{15}$ is amino, monosubstituted amino and disubstituted amino and can be substituted with alkyl, cycloalkyl, alkenyl, substituted alkenyl, alkynyl, substituted alkynyl, aralkyl, substituted aralkyl, aryl, substituted aryl, heterocycle and substituted hetereocycle;

R$_{16}$ is oxygen, and R$_{19}$ is hydrogen.

Formula I compounds prepared by the present invention are useful in preventing or treating diseases or conditions associated with platelet aggregation and/or platelet activation; such diseases include venous thrombosis, thrombophlebitis, arterial embolism, coronary and cerebral arterial thrombosis, unstable angina, myocardial infarction, stroke, cerebral embolism, kidney embolisms and pulmonary embolisms.

In one embodiment, the invention provides a pharmaceutical formulation comprising a compound of Formula I and a pharmaceutically acceptable carrier. Pharmaceutically acceptable carriers can be selected by those skilled in the art using conventional criteria. Pharmaceutically acceptable carriers include, but are not limited to, saline solution, aqueous electrolyte solutions, isotonicy modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, polysaccharides such as dextrans, and glycosaminoglycans such as sodium hyaluronate and salts such as sodium chloride and potassium chloride.

Preparation of Formula I Compounds.

The process of the present invention can be used to prepare a compound of general Formula I, Ia, IX, X, XI, and XII; which can be the final product or it can be used as an intermediate and further modified to a desired product.

Scheme 1 provides the general synthesis for the compound of Formula XII, phosphoric acid mono-(2-substituted-6-ureidosubstituted-tetrahydro-furo[3,4-d][1,3]dioxol-4-ylmethyl)ester salts, trans isomer. In Scheme 1, a compound of Formula II is prepared first, then chemically decomposed to its trans isomer of Formula Ia. Formula Ia serves as an intermediate, which is further derivatized and modified to a final product of Formula XII.

Alternatively, a mixture of cis and trans isomers of phosphoric acid mono-(2-substituted -6-ureidosubstituted-tetrahydro-furo[3,4-d][1,3]dioxol-4-ylmethyl)ester salts can be prepared first, for example, by steps 1, and 3-7. The mixture is then subjected to chemical decomposition (step 2) to form a trans isomer of Formula XII.

Scheme 2 provides a specific example of Scheme 1, for the preparation of trans-phosphoric acid mono-{6-[6-(3-ethylureido)-purin-9-yl]-2-styryl-tetrahydro-furo[3,4-d][1,3]dioxol-4-ylmethyl}ester bis sodium salt.

Schemes 1 and 2 are meant to be illustrative of the present invention, and are not to be taken as limiting thereof. Those having skill in the art will recognize that the starting materials can be varied and additional steps can be employed to produce compounds encompassed by the present invention. In some cases, protection of certain reactive functionalities may be necessary to achieve some of the above transformations. In general, the need for such protecting groups as well as the conditions necessary to attach and remove such groups will be apparent to those skilled in the art of organic synthesis.

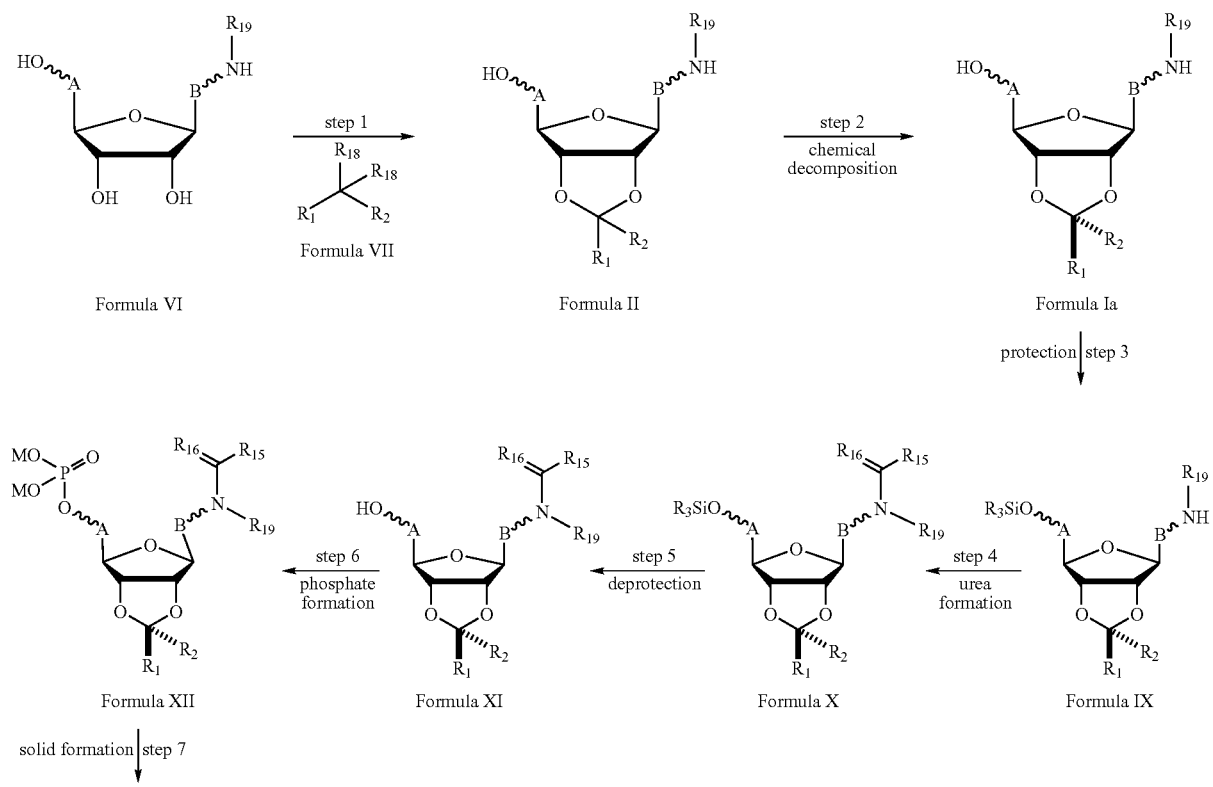

Scheme 1

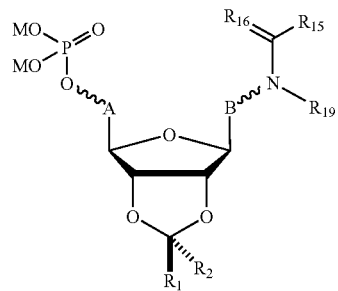
Formula XII solid
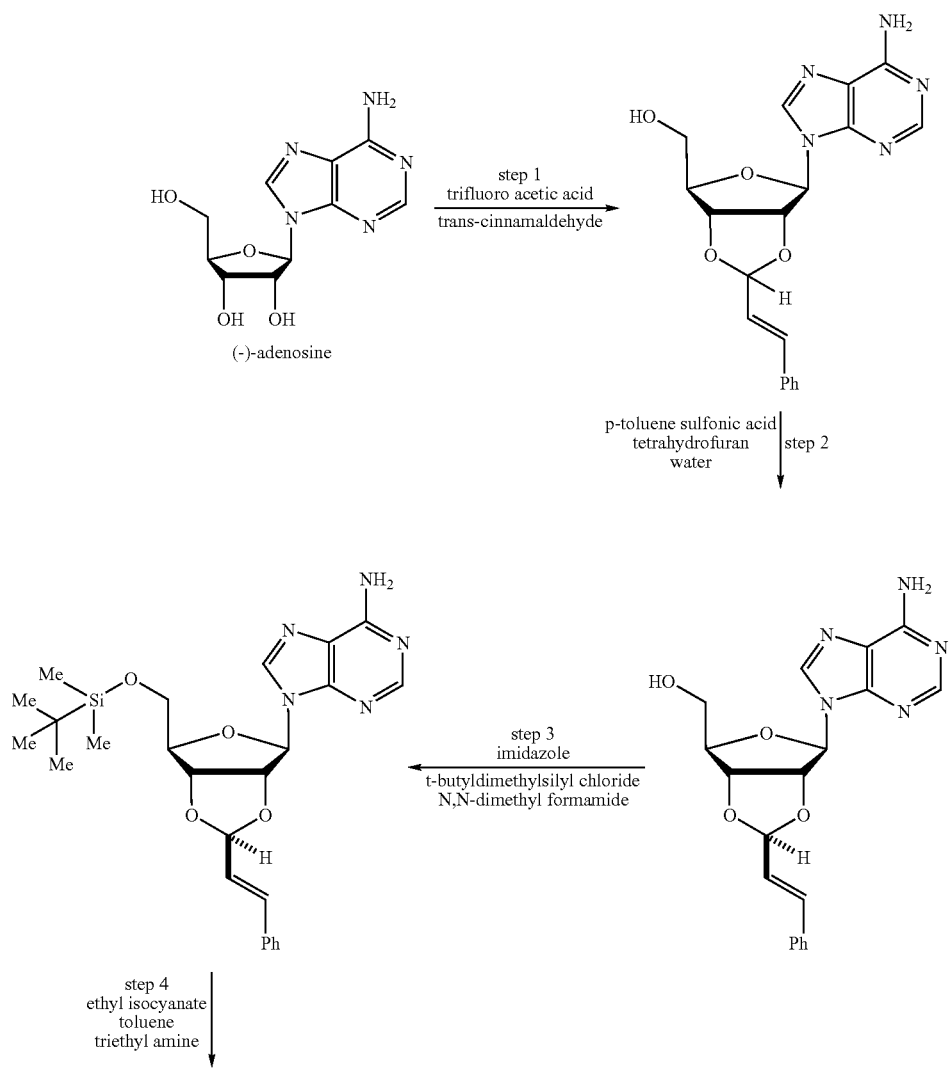

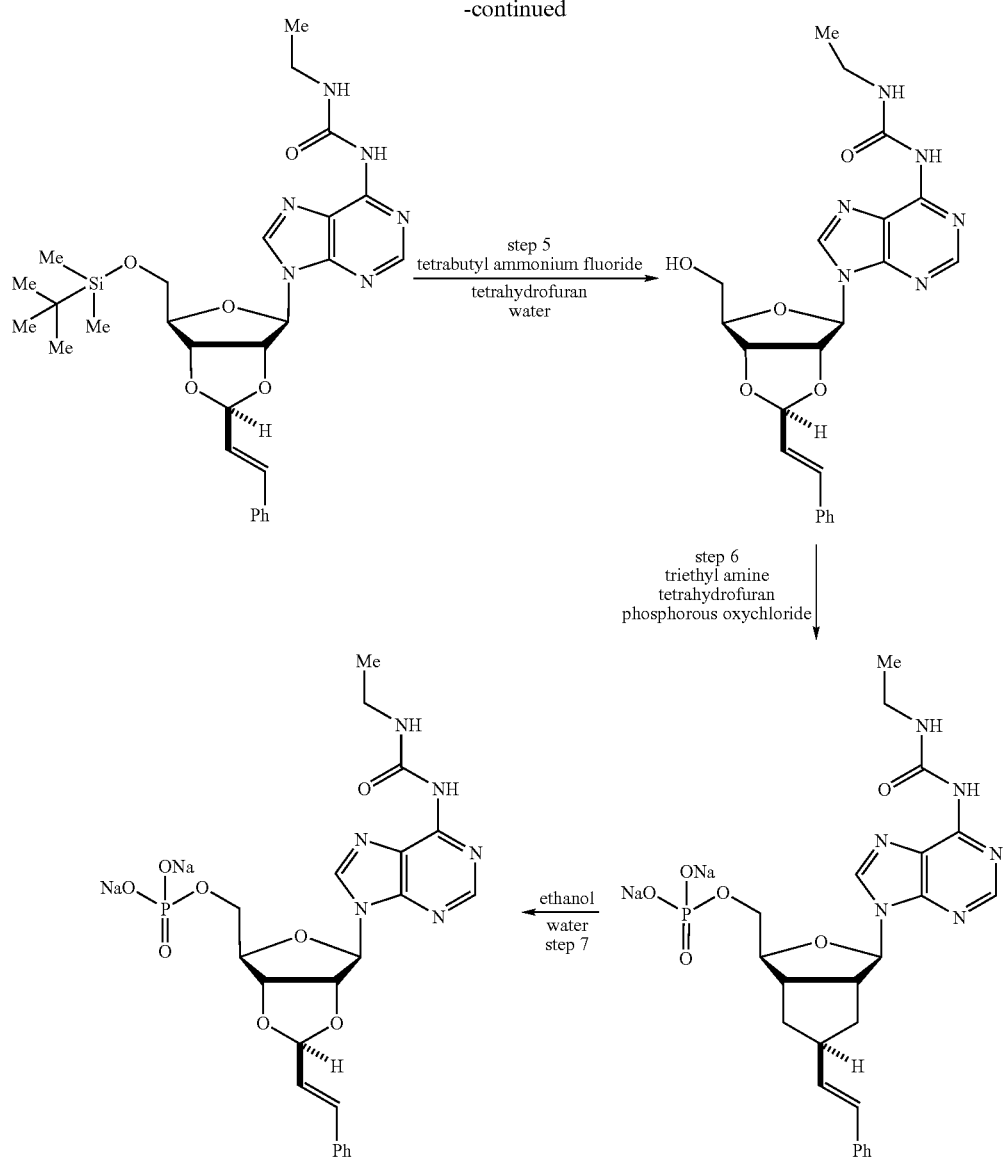

-continued

Steps 1 and 2

Steps 1 and 2 follow the same procedures as described above for the preparation of a compound of Formula II and for chemical decomposition of a compound of Formula II.

Step 3

A compound of formula (II) and a suitable solvent system are charged to a reaction vessel. The order of addition can be compelled by convenience, or by other process issues familiar to the artisan of process chemistry. While the reaction can be conducted in numerous solvents: carbon tetrachloride, chloroform, dichloromethane, 1,1-dichloroethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, dimethylformamide (DMF), dimethylacetamide (DMAC), N-methylpyrrolidinone (NMP), formamide, N-methylacetamide, N-methylformamide, acetonitrile (ACN), dimethylsulfoxide, propionitrile, sulfolane, N,N-dimethylpropionamide, and hexamethylphosphoramide; the preferred solvents are dimethylformamide (DMF), dimethylacetamide (DMAC), and acetonitrile (ACN). A preferred solvent is dimethylformamide (DMF). In circumstances when the formula (II) compound requires drying (removal of water), a solvent that assists by azeotropic removal of water can be used. Ethyl acetate, isopropyl acetate or t-butyl acetate is preferred. The charging of the starting formula (II) and the appropriate solvent is preferably followed by an excess of base. Typical bases are imidazole, pyridine, N,N-diethylaniline; triethylamine, N-methylmorpholine (NMM), N,N-diisopropylethylamine, N,N-diethylcyclohexylamine, N,N-dimethylcyclohexylamine, N,N,N'-triethylenediamine, N,N-dimethyloctylamine; 1,5-diazabicyclo[4.3.0]non-5-ene (DBN); 1,4-diazabicyclo[2.2.2]octane (DABCO); 1,8-diazabicyclo[5.4.0]undec-7-ene (DBU); tetramethylethylenediamine (TMEDA); and substituted pyridines such as N,N-dimethylaminopyridine (DMAP), 4-pyrrolidinopyridine, and 4-piperidinopyridine. Additionally, suitable bases can be selected from polymeric tertiary amines, as well as polymeric aromatic amines. A preferred base is imidazole. The charging of the base is followed by the addition of an appropriate silylating reagent. Preferred silylating reagents are t-butyl dimethyl silyl chloride, t-butyl dimethyl silyl trifluoromethyl sulfonate, trimethyl silyl chloride, triethyl silyl chloride, trimethyl silyl trifluoromethyl sulfonate, triethyl silyl trifluoromethyl sulfonate. A preferred silylating reagent is t-butyl dimethyl silyl chloride. The amount of base and silylating reagent is typically based on the molar equivalents of formula (Ia), and is preferably 1.0-2.0 and 1.0-2.0 molar equivalents, respectively. The amount of base is typically in slight molar excess in relation to the amount of silylating reagent. The formation of formula (IX) is preferably done between −10 to 25° C. The reaction is preferably monitored by HPLC, and is considered complete when the area of the product is <1% in relation to the starting formula (II). Depending on the starting solvents and temperature, the reaction is generally done in 1-12 hours. The reaction can be quenched and the product crystallized by diluting with an antisolvent mixture. Suitable antisolvent mixtures are aqueous solutions of methanol, ethanol, 1-propanol, 2-propanol, 1-butanol, 2-butanol, i-butyl alcohol, t-butyl alcohol, 1-, 2-, or 3-pentanol, neo-pentyl alcohol, t-pentyl alcohol and cyclohexanol; with an aqueous solution of 2-propanol being preferred. The proportion of water in the antisolvent mixture is 65-85 weight percent. The amount of antisolvent mixture is typically based on the amount of reaction solvent. The proportion of antisolvent mixture is 50-65 volume percent. The product of formula (IX) is isolated, preferably by filtration of the organic phase. The solid can be rinsed with the organic constituent of the antisolvent mixture. The product is preferably dried under vacuum preferably at a temperature in the range 30 to 60° C., to constant weight.

Step 4

A compound of formula (IX) and a suitable solvent system are preferably charged to a reaction vessel. The order of addition can be compelled by convenience, or by other process issues familiar to the artisan of process chemistry. While the reaction can be conducted in numerous solvents: carbon tetrachloride, chloroform, o-dichlorobenzene, chlorobenzene, fluorobenzene, benzene, toluene, ethylbenzene, in-, o-, or p-xylene, tetrahydrofrran, 1,4-dioxane, ethylene glycol dimethyl ether, ethylene glycol diethyl ether, diethylene glycol dimethyl ether, diethylene glycol diethyl ether, triethylene glycol diisopropyl ether, anisole, t-butyl methyl ether, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DM1), N-methylpyrrolidinone (NMP), formamide, N-methylacetamide, N-methylformamide, acetonitrile (ACN), dimethylsulfoxide, propionitrile, sulfolane, N,N-dimethylpropionamide, nitrobenzene, and hexamethylphosphoramide; preferred solvents are benzene and toluene. The charging of the starting formula (IX) and the appropriate solvent is preferably followed by an excess of base and an appropriate amount of an isocyanate. The order of addition can be compelled by convenience, or by other process issues familiar to the artisan of process chemistry. Typical bases are pyridine, N,N-diethylaniline; triethylamine, N-methylmorpholine (NMM), N,N-diisopropylethylamine, N,N-diethylcyclohexylamine, N,N-dimethylcyclohexylamine, N,N,N'-triethylenediamine, N,N-dimethyloctylamine; 1,5-diazabicyclo[4.3.0]non-5-ene (DBN); 1,4-diazabicyclo[2.2.2]octane (DABCO); 1,8-diazabicyclo[5.4.0]undec-7-ene (DBU); tetramethylethylenediamine (TMEDA); and substituted pyridines such as N,N-dimethylaminopyridine (DMAP), 4pyrrolidinopyridine, and 4-piperidinopyridine; with a preferred base being triethylamine. The amount of base and isocyanate is typically based on the molar equivalents of formula (IX), and is preferably 1.0-2.0 and 1.0-4.0 molar equivalents, respectively. The amount of base is typically in slight molar excess in relation to the amount of formula (IX). The formation of formula (X) is preferably done between 25 to 120° C, more preferably from 55 to 120° C. The reaction is preferably monitored by HPLC, and is considered complete when the area of ihe product is <1% in relation to the starting formula (IX). Depending on the starting solvents and temperature, the reaction is generally done in 12-72 hours. The excess isocyanate reagent can be removed by the addition of additional reaction solvent, preferably an equal portion to the starting volume, and subsequent distillation of this portion from the reaction vessel. The product can be crystallized by diluting with an antisolvent. Suitable antisolvents are cyclohexane, pentane, hexane, cycloheptane, methylcyclohexane, heptane, octane, indane and nonane; with heptane being preferred. The amount of antisolvent is typically based on the amount of reaction solvent. The proportion of antisolvent is 70-90 volume percent. The product of formula (X) is isolated, preferably by filtration of the organic phase. It can be rinsed with the antisolvent. The product is preferably dried under vacuum preferably at a temperature in the range 30 to 60° C, to constant weight.

Step 5

A compound of formula (X) and a suitable solvent system are preferably charged to a reaction vessel. The order of addition can be compelled by convenience, or by other process issues familiar to the artisan of process chemistry. While the reaction can be conducted in numerous solvents: carbon tetrachloride, chloroform, dichloromethane, benzene, toluene, ethylbenzene, m-, o-, or p-xylene, tetrahydrofuran, 1,3-dioxane, 1,4-dioxane, diethyl ether, ethylene glycol dimethyl ether, ethylene glycol diethyl ether, diethylene glycol dimethyl ether, diethylene glycol diethyl ether, triethylene glycol diisopropyl ether, anisole, t-butyl methyl ether, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide, propionitrile, methyl acetate, ethyl acetate, isopropyl acetate, t-butyl acetate, sulfolane, N,N-dimethylpropionamide, and hexamethylphosphoramide; the preferred solvents are tetrahydrofuran, 1,4-dioxane and dimethylformamide (DMF). The charging of the starting formula (X) and the appropriate solvent is preferably followed by an excess of a suitable fluoride source. Suitable fluoride sources are tetrabutyl ammonium fluoride, tetra ethyl ammonium fluoride, pyridine hydrogen fluoride, hydrogen fluoride, triethylamine hydrogen fluoride, ammonium fluoride, potassium fluoride, cesium fluoride. A preferred fluoride source is tetrabutyl ammonium fluoride. The amount of fluoride source is typically based on the molar equivalents of formula (X), and is preferably 1.0-2.0 molar equivalents. The formation of formula (XI) is preferably done between 25 to 80° C. The reaction is preferably monitored by HPLC, and is considered complete when the area of the product is <1% in relation to the starting formula (X). Depending on the starting solvents and temperature, the reaction is generally done in 2-24 hours. The reaction can be quenched by the addition of an aqueous acid solution. These include, but are not limited to mineral acids such as hydrochloric acid, hydrobromic acid, hydroiodic acid, sulfuric acid, nitric acid, phosphoric acid; and organic acids such as formic acid, acetic acid, methanesulfonic acid, trifluoroacetic acid, propionic acid, butyric acid, valeric acid, caproic acid, oxalic acid, benzenesulfonic acid, and p-toluenesulfonic acid. Additionally, aqueous acid includes sodium bisulfate, potassium bisulfate, ammonium chloride, lithium bisulfate and the like. An aqueous hydrochloric acid solution is preferred. The addition of the aqueous acid can be monitored by pH. The pH of the resulting quenched reaction is preferably between 6.0-7.5. The product can be crystallized by the addition of an antisolvent; with water being preferred. The product of formula (XI) is isolated, preferably by filtration of the organic phase. The solid can be rinsed with a solvent: methanol, ethanol, 1-propanol, 2-propanol, 1-butanol, 2-butanol, i-butyl alcohol; with ethanol and 2-propanol being preferred. The product is preferably dried under vacuum preferably at a temperature in the range 30 to 60° C., to constant weight.

Step 6

A compound of formula (XI) and a suitable solvent are preferably charged to a reaction vessel. The order of addition can be compelled by convenience, or by other process issues familiar to the artisan of process chemistry. While the reaction can be conducted in numerous solvents such as: chloroform, dichloromethane, 1,1-dichloroethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, dimethylformamide (DMF), dimethylacetamide (DMAC), N-methylpyrrolidinone (NMP), formamide, N-methylacetamide, N-methylformamide, acetonitrile (ACN), dimethylsulfoxide, propionitrile, sulfolane, N,N-dimethylpropionamide, and hexamethylphosphoramide, the preferred solvents are dimethylformamide (DMF), dimethylacetamide (DMAC), and acetonitrile (ACN) and trimethyl phosphate; the preferred solvent is tetrahydrofuran. The charging of the starting formula (XI) and the appropriate solvent is preferably followed by an excess of base. Typical bases are pyridine, N,N-diethylaniline; triethylamine, N-methylmorpholine (NMM), N,N-diisopropylethylamine, N,N-diethylcyclohexylamine, N,N-dimethylcyclohexylamine, N,N,N'-triethylenediamine, N,N-dimethyloctylamine; 1,5-diazabicyclo[4.3.0]non-5-ene (DBN); 1,4-diazabicyclo[2.2.2]octane (DABCO); 1,8-diazabicyclo[5.4.0]undec-7-ene (DBU); tetramethylethylenediamine (TMEDA); and substituted pyridines such as N,N-dimethylaminopyridine (DMAP), 4pyrrolidinopyridine, and 4-piperidinopyridine. Additionally, suitable bases can be selected from polymeric tertiary amines, as well as polymeric aromatic amines. A preferred base is triethylamine. The charging of the base is followed by the addition of an appropriate phosphorylating reagent. Typical phosphorylating reagents are phosphorous oxycliloride, methoxyphosphoryl dichloride, phenoxyphosphoryl dichloride and 2-chloro-4H-1,3,2-dioxaphosphorin-4-one. A more preferred phosphorylating reagent being phosphorous oxychloride. The amount of base and phosphorylating reagent is typically based on the molar equivalents of formula (XI), and is preferably 1.0-2.0 and 1.0-3.0 molar equivalents, respectively. The amount of base is typically in molar excess in relation to the amount of phosphorylating reagent. It can be advantageous to monitor the temperature during the addition of the phosphorylating reagent to prevent loss in yield. The formation of formula (XII) is preferably done between -10 to 25° C. The reaction is preferably monitored by HPLC, and is considered complete when the area of the product is <5% in relation to the starting formula (XI). Depending on the starting solvents and temperature, the reaction is generally done in 1-24 hours. The reaction can be quenched by adding it to an aqueous base solution. Examples of such base solutions include sodium, lithium, and potassium salts of carbonates; sodium, lithium, and potassium salts of bicarbonates; and sodium, lithium and potassium salts of hydroxides, with sodium hydroxide being preferred. It is advantageous to monitor the temperature during the addition of the reaction mixture to the aqueous base solution to prevent loss in yield and the production of unwanted by-products. The temperature of the aqueous base solution is preferably maintained between 0 and 20° C during the addition process. The compound of formula (XII) is isolated, preferably by filtration or centrifugation. The solid can be rinsed with a solvent: methanol, ethanol, 1-propanol, 2-propanol, 1-butanol, 2-butanol, and i-butyl alcohol; with ethanol and 2-propanol being preferred. The most preferred being ethanol. The product is preferably dried under vacuum preferably at a temperature in the range 25 to 60° C, until the measured water content is from 1 to 20 weight percent.

Step 7

A compound of formula (XII) and a suitable solvent mixture are preferably charged to a reaction vessel. The order of addition can be compelled by convenience, or by other process issues familiar to the artisan of process chemistry. This step can be conducted in numerous aqueous solvent systems; the organic solvent being: methanol, ethanol, 1-propanol, 2-propanol, 1-butanol, 2-butanol, and i-butyl alcohol; with ethanol and 2-propanol being preferred. The most preferred being ethanol. The amount of water in the aqueous solvent solution is preferably 30 to 80%. The amount of aqueous solvent is typically based on the weight of the starting formula (XII) solid. The amount of aqueous solvent preferably being 15-30 fold in excess of the weight of starting formula (XII). Dissolution of the solid can be facilitated by heat. The dissolution is preferably performed between 40 to 60° C. Generation of solid can be facilitated by cooling. The generation of solid is preferably performed between 0 to 30° C. The compound of formula (XII) is isolated, preferably by filtration or centrifugation. The solid can be rinsed with a solvent: methanol, ethanol, 1-propanol, 2-propanol, 1-butanol, 2-butanol, and i-butyl alcohol; and/or and aqueous solution of said solvent, with ethanol and 2-propanol being preferred. The most preferred being ethanol. The product is preferably dried under vacuum preferably at a temperature in the range 25 to 60° C., until the measured water content is from 1 to 10 weight percent. These solids can be monitored by KF, DSC, XRD, HPLC and IC to assure formation of suitable quality material.

Alternately, a compound of formula (XII) and water are preferably charged to a reaction vessel. The order of addition can be compelled by convenience, or by other process issues familiar to the artisan of process chemistry. The amount of water is preferably based on the weight of the starting formula (XII) is preferably 8-12 fold in excess. Dissolution of the solid can be facilitated by heat. The dissolution is preferably performed between 40 to 60° C. Generation of solid can be facilitated by the addition of an organic solvent. The organic solvent being: methanol, ethanol, 1-propanol, 2-propanol, 1-butanol, 2-butanol, and i-butyl alcohol; with ethanol and 2-propanol being preferred. The most preferred being ethanol. The amount of solvent is typically based on the weight of the starting formula (XII) solid. The amount of solvent preferably being 8-12 fold in excess of the weight of starting formula (XII). The addition of the organic solid can be performed between 0 to 60° C. The generation of solid is preferably performed between 0 to 30° C. The compound of formula (XII) is isolated, preferably by filtration or centrifugation. The solid can be rinsed with a solvent: methanol, ethanol, 1-propanol, 2-propanol, 1-butanol, 2-butanol, and i-butyl alcohol; with ethanol and 2-propanol being preferred. The most preferred being ethanol. The product is preferably dried under vacuum preferably at a temperature in the range 25 to 60° C., until the measured water content is from 1 to 10 weight percent. These solids can be monitored by KF, DSC, XRD, HPLC and IC to assure formation of suitable quality material.

The present invention is also directed to a process for preparing a compound of Formula XII,

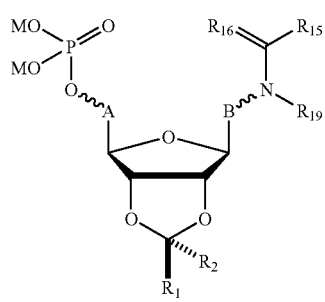

Formula XII comprising the steps of:

(a) preparing a compound of Formula I, wherein A is CH$_2$OH, B is a purine residue as in Formula III;

(b) reacting the compound of Formula I with a silylating agent to form a compound of Formula IX,

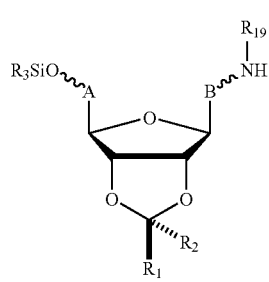

Formula IX wherein R$_{19}$ is H, alkyl, cycloalkyl, aryl, arylalkyl, heterocycloalkyl, or heteroarylalkyl;

(c) reacting the compound of Formula IX with an isocyanate R$_{15}$—N=C=R$_{16}$ to form a compound of Formula X, wherein R$_{15}$ and R$_{16}$ are defined previously,

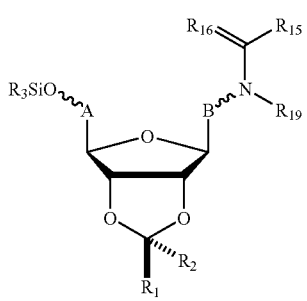

Formula X (d) reacting the compound of Formula X with a deprotecting reagent selected from the group consisting of (R$_{17}$)$_4$N$^+$F$^-$, MF, and R$_{18}$H$^+$F$^-$ to form a compound of Formula XI;

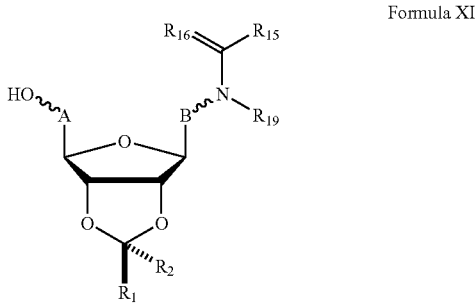

Formula XI wherein R$_{17}$ is independently H, alkyl, cycloalkyl, aryl, or heteroaryl;

M is hydrogen, NH$_4^+$, Na$^+$ or other pharmaceutically acceptable inorganic or organic counterions; and R$_{18}$ is a heteroaryl amine with at least one nitrogen in the aryl ring; and (e) reacting the compound of Formula XI with a phosphorylating agent;

whereby a compound of Formula XII is prepared.

In one embodiment of the above process, R$_2$ is H and R$_1$ is styryl. In another embodiment, R$_{19}$ is H. In yet another embodiment, R$_{16}$ is oxygen and R$_{15}$ is monosubstituted amino such as alkylamino, e,g., ethylamino.

In one embodiment of the above process, the deprotecting agent is a tetraalkylammonium fluoride or a trialkylhydrogenammonium fluoride, the isocyanate is ethyl isocyanate, and the phosphorylating agent is phosphorous oxychloride.

The invention is illustrated further by the following examples that are not to be construed as limiting the invention in scope to the specific procedures described in them.

EXAMPLES

Example 1

Preparation of cis-[6-(6-Amino-purin-9-yl)-2-styryl-tetrahydro-furo[3,4-d][1,3]dioxol-4-yl]-methanol and trans-[6-(6-Amino-purin-9-yl)-2-styryl-tetrahydro-furo[3,4-d][1,3]dioxol-4-yl]-methanol (Scheme 2, Step 1)

A 3 L flask equipped with a mechanical stirrer, addition funnel, internal temperature monitor and nitrogen inlet was flushed with nitrogen and charged with 90 g of (−)-adenosine and 0.339 L of trans-cinnamaldehyde. After cooling (acetone/wet ice bath) to −5° C., 0.403 L of trifluoroacetic acid was added keeping the temperature between −5° C. and +5° C. The reaction was stirred at 0° C. until 80% conversion is achieved (approximately 2 hours, as measured by HPLC). The reaction was then diluted with 1.1 L of iso-propyl acetate maintaining a reaction temperature of <5° C. The reaction was then quenched with 0.810 L of 5 N sodium hydroxide maintaining a reaction temperature of 20° C. to 25° C. During this quench, the product crystallized and two layers were formed. After the addition was complete, agitation was stopped and the layers were allowed to separate. The product settled into the bottom of the top organic phase. The lower aqueous phase was decanted and agitation was continued. The product was isolated by filtration and washed with 3×0.450 L of iso-propyl acetate. The resulting solid was dried on a filter and then transferred to an oven and dried to a constant weight under vacuum at 50° C. Approximately 85-90 g of a mixture of cis-[6-(6-Amino-purin-9-yl)-2-styryl-tetrahydro-furo[3,4-d][1,3]dioxol-4-yl]-methanol and trans-[6-(6-Amino-purin-9-yl)-2-styryl-tetrahydro-furo[3,4-d][1,3]dioxol-4-yl]-methanol was obtained.

Example 2

Preparation of trans-[6-(6-Amino-purin-9-yl)-2-styryl-tetrahydro-furo[3,4-d][1,3]dioxol-4-yl]-methanol (Scheme 2, Step 2)

A 1 L flask equipped with a mechanical stirrer, addition funnel, internal temperature monitor and nitrogen inlet was flushed with nitrogen and charged with 50 g of a 1.5:1 mixture of trans:cis-[6-(6-amino-purin-9-yl)-2-styryl-tetrahydro-furo[3,4-d][1,3]dioxol-4-yl]-methanol, 18.6 g of p-toluenesulfonic acid, 0.2 L of tetrahydrofuran and 0.050 L of water. The reaction was warmed to 50° C and stirred until the HPLC area % ratio of trans-[6.-(6-amino -purin-9-yl)-2-styryl-tetrahydro-furo[3,4-d][1,3]dioxol-4-yl]-methanol to cis-[6-(6-amino-purin-9-yl)-2-styryl-tetrahydro-furo[3,4-d][1,3]dioxol-4-yl]-methanol was <99:1.0. The reaction was then quenched with 0.150 L of 2 sodium hydroxide and stirred for 10 minutes. Agitation was stopped and the phases allowed to separate. The lower aqueous phase was decanted and agitation was continued. The reaction was then diluted with 0.200 L of iso-propyl acetate and allowed to cool to 20° C. The product was isolated by filtration and washed with 0.2 L of iso-propyl acetate. The resulting paste was dried on a filter until it was tractable enough to manipulate. The cake cracked and separated and required pressing to invoke further solvent removal. The resulting solid was dried on a filter and then transferred to an oven and dried to a constant weight under vacuum at 50° C. Approximately 19 g of trans-[6-(6-Amino-purin-9-yl)-2-styryl-tetrahydro-furo [3,4-d][1,3]dioxol-4-yl]-methanol was obtained. This example demonstrates the preparation of a single acetal isomer.

HPLC Method: Column: Phenomenex Synergi Polar RP, 4 μm, 80 angstrom, 150×3.0 mm; Mobile Phase: 25 mM ammonium acetate buffer, pH=5: acetonitrile (75:25); Detection: UV, 254 nm; Column temperature: 35° C.; Injection Volume: 10 μL; Flow Rate: 1.5 mL/min; Run Time: 16 minutes; Typical Retention Times (RT) and Relative Retention Times (RRT): (−)-adenosine (RT=0.70 min, RRT=0.06), trans-cinnamaldehyde (RT=7.35 min, RRT=0.67), trans-[6-(6-amino-purin-9-yl)-2-styryl-tetrahydro-furo[3,4-d][1,3]dioxol-4-yl]-methanol (RT=9.92 min, RRT=0.90), cis-[6-(6-amino-purin-9-yl)-2-styryl-tetrahydro-furo[3,4-d][1,3]dioxol-4-yl]-methanol (RT=10.99 min, RRT=1.00).

$^1$H NMR (300 MHz, D$_2$O) δ 3.83 (m, 1H), 4.02 (d, 1H), 4.53 9d, 1H), 5.18 (m, 1H), 5.32 (t, 1H), 5.67 (s, 2H), 5.96 (t, 2H), 6.11 (m, 2H), 6.81 (d, 1H), 7.36 (m, 5H), 7.88 (s, 1H), 8.34 (s, 1H).

MS (ES): m/z 380.3 (M−H).

Example 3

Preparation of trans-9-[6-(tert-Butyl-dimethyl-silanyloxymethyl)-2-styryl-tetrahydro-furo[3,4-d][1,3] dioxol-4-yl]-9H-purin-6-ylamine (Scheme 2, Step 3)

A 3 L flask equipped with a mechanical stirrer, addition funnel, internal temperature monitor, nitrogen inlet and vacuum line was flushed with nitrogen and charged with 100 g of trans-[6-(6-amino-purin-9-yl)-2-styryl-tetrahydro-furo [3,4-d][1,3]dioxol-4-yl]-methanol and 2 L of iso-propyl acetate. The reaction was warmed to reflux and 0.600 L of distillate was collected. The reaction was then charged with 1.0 L of N,N-dimethyl formamide and distillate was collected until a pot temperature of 100° C. was reached at a pressure of 200 torr. The reaction was then cooled to 20° C. The reaction was then charged with 0.0223 kg of imidazole and 0.0474 kg of tert-butyl dimethyl silyl chloride. After stirring for two hours the reaction was tested for completeness by HPLC. The reaction was then quenched with 1.4 L of a 2.5:1 mixture of water/2-propanol keeping the internal temperature between 15-20° C. After stirring for 1 hour the product was isolated by filtration and washed with 1.2 L of 2-propanol. The solid was dried to constant weight in a vacuum oven at 50° C. Approximately 105 g of trans-9-[6-(tert-Butyl-dimethyl-silanyloxymethyl)-2-styryl-tetrahydro-furo[3,4-d][1,3]dioxol-4-yl]-9H-purin-6-ylamine was obtained.

MS (ES): m/z 494.4 (M−H).

Example 4

Preparation of trans-1-{9-[6-(tert-Butyl-dimethyl-silanyloxymethyl)-2-styryl-tetrahydro-furo[3,4-d][1,3]dioxol-4-yl]-9H-purin-6-yl}-3-ethyl-urea (Scheme 2, Step 4)

A 2 L flask equipped with a mechanical stirrer and reflux condenser was flushed with nitrogen and charged with 0.088 kg of trans-9-[6-(tert-butyl-dimethyl-silanyloxymethyl)-2-styryl-tetrahydro-furo[3,4-d][1,3]dioxol-4-yl]-9H-purin-6-ylamine, 0.352 L of toluene, 0.0454 L of ethyl isocyanate and 0.0247 L of triethylamine. The reaction was warmed to 60° C. The reaction was run for 40 hours and then assayed for completeness. The reaction was diluted with 0.300 L of toluene and 0.380 L of distillate was collected. The reaction was cooled to 100° C and 0.881 L of heptane was added slowly. The resulting temperature was 55° C. The product crystallized upon cooling to room temperature. It was then isolated by filtration and washed with 2×0.2 L of heptane. The solid was dried to a constant weight in a vacuum oven at <50° C. Approximately 0.040 Kg of trans-1-{9-6-(tert-Butyl-dimethyl-silanyloxymethyl)-2-styryl-tetrahydro-furo[3,4-d][1,3]dioxol-4-yl]-9H-purin-6-yl }-3-ethyl-urea was obtained.

MS (ES): m/z 565.5 (M−H).

Example 5

Preparation of trans-1-Ethyl-3-[9-(6-hydroxymethyl-2-styryl-tetrahydro-furo[3,4-d][1,3]dioxol-4-yl)-9H-purin-6-yl]-urea (Scheme 2, Step 5)

A 2 L flask equipped with a mechanical stirrer was flushed with nitrogen and charged with 0.094 kg of trans-1-{9-[6-(tert-Butyl-dimethyl-silanyloxymethyl)-2-styryl-tetrahydro-furo[3,4-d][1,3]dioxol-4-yl]-9H-purin-6-yl}-3-ethyl-urea and 0.0235 L of THF. Tetrabutyl ammonium fluoride (0.249 L of a 1 M solution in THF solution) was then added and the reaction stirred until complete by HPLC. A solution of 0.047 L of 1 N hydrochloric acid and 0.191 L of water was then added. The product crystallized upon stirring at 20° C. The solid was then isolated by filtration and washed with 2×0.500 L of 2-propanol. The solid was dried to a constant weight in a vacuum oven at <50° C. Approximately 0.062 kg of trans-1-Ethyl-3-[9-(6-hydroxymethyl-2-styryl-tetrahydro-furo[3,4-d][1,3]dioxol-4-yl) -9H-purin-6-yl]-urea was obtained. This Example demonstrates the preparation of a fully elaborated nucleoside prior to phosphorylation.

$^1$H NMR (300 MHz, $D_2O$) δ 1.29 (t, 3H), 3.46 (m, 2H), 3.85 (m, 1H), 4.02 (d, 1H), 4.56 (s, 1H), 5.25 (m, 3H), 5.92 (d, 1H), 6.15 (m, 2H), 6.82 (d, 1H), 7.34 (m, 5H), 8.52 (d, 2H), 9.18 (s, 1H), 9.54 (t, 1H).

MS (ES): m/z 451.2 (M−H).

Example 6

Preparation of trans-Phosphoric acid mono-{6-[6-(3-ethyl-ureido)-purin-9-yl]-2-styryl-tetrahydro-furo[3,4-d][1,3]dioxol-4-ylmethyl}ester bis sodium salt (Scheme 2, Step 6)

A 5 L flask (Flask A) equipped with a mechanical stirrer, addition funnel, internal temperature monitor and nitrogen inlet was flushed with nitrogen and charged with 0.095 g of trans- 1-ethyl-3-[9-(6-hydroxymethyl-2-styryl-tetrahydro-furo[3,4-d][1,3]dioxol-4-yl)-9H-purin -6-yl]-urea, 0.0321 g of triethylamine and 2.85 L of tetrahydrofuran. The white slurry was cooled to 0-2° C. A solution of 0.0451 g of phosphorous oxychloride in 0.095 L of tetrahydrofuran was added in one portion and the reaction stirred for two hours. A separate 5 L flask (Flask B) equipped with a mechanical stirrer, addition funnel, internal temperature monitor and nitrogen inlet was flushed with nitrogen and charged with 0.987 L of 1 N sodium hydroxide and the contents cooled to 0-5° C. The contents of Flask A were slowly transferred to Flask B over a minimum of one hour while maintaining an internal temperature in Flask B of <10° C. The pH of the resulting solution was adjusted to 10 with 0.015 L of 5 N sodium hydroxide. The product crystallized upon stirring at 0° C. It was then isolated by filtration and washed with 1×0.950 L of a 50% aqueous ethanol solution. The solid was dried to a constant weight in a vacuum oven at <50° C. Approximately 0.082 kg of trans-Phosphoric acid mono-{6-[6-(3-ethyl -ureido)-purin-9-yl]-2-styryl-tetrahydro-furo[3,4-d][1,3 ]dioxol-4-ylmethyl}ester bis sodium salt was obtained.

Example 7

Preparation of trans-Phosphoric acid mono-{6-[6-(3-ethyl-ureido)-purin-9-yl]-2-styryl-tetrahydro-furo[3,4-d][1,3]dioxol-4-ylmethyl}ester bis sodium salt (Scheme 2, Step 7)

A 1 L flask equipped with a mechanical stirrer and reflux condenser was charged with 0.082 kg of crude trans-phosphoric acid mono-{6-[6-(3-ethyl-ureido)-purin-9-yl]-2-styryl-tetrahydro-furo[3,4-d][1,3]dioxol-4-ylmethyl} bis sodium salt and 0.820 L of water. The slurry was warmed to 50° C. The solution was cooled to 20° C. and filtered through a bed of celite. The resulting solution was further clarified by filtering through a 0.45 □m filter. A 2 L flask equipped with a mechanical stirrer was charged with the above solution of trans-phosphoric acid mono-{6-[6-(3-ethyl-ureido)-purin-9-yl]-2-styryl-tetrahydro-furo[3,4-d][1,3]dioxol-4-ylmethyl} bis sodium salt. This solution was charged with 1.23 L of ethanol and stirred for one hour. The product was then isolated by filtration and washed with 1×0.082 L of a 60% aqueous ethanol solution. The solid was dried to a constant weight in a vacuum oven at <50° C. Approximately 0.049 kg of trans-phosphoric acid mono-{6-[6-(3-ethyl-ureido)-purin-9-yl]-2-styryl-tetrahydro-furo[3,4-d][1,3]dioxol-4-ylmethyl} bis sodium salt was obtained.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed:

1. A process for preparing a compound of Formula I, or a pharmaceutically acceptable salt, solvate, hydrate, or tautomer thereof,

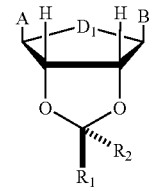

Formula I comprising the steps of:

(a) obtaining compounds of Formula II, which is a mixture of cis and trans-diastereomers, wherein cis and trans refer to the positions of $R_2$ vs. the two hydrogens on the 4 and 5 positions of the dioxolane ring;

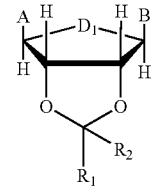

Formula II (b) reacting the mixture with a solution comprising a solvent and an acid that is a hydrogen donor or an electron pair acceptor, whereby the cis diastereomer is decomposed and the compound of Formula I is obtained;

wherein $D_1$ is $CH_2$, $NR_3$, O, or S;

$R_2$=H;

$R_1$ and $R_3$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, aralkyl, substituted aralkyl, heterocyclyl, and substituted heterocyclyl, with the proviso that $R_1$ and $R_2$ are not both hydrogen on the dioxolane ring;

A is

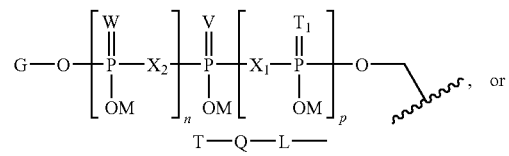

wherein;
  n and p are 0, 1,or 2 such that the sum of n+p is from 0 to 3;
  each M is independently hydrogen, $NH_4^+$, $Na^+$ or another pharmaceutically acceptable inorganic or organic counterion;
  $T_1$, V and W are each independently O or S;
  $X_1$ and $X_2$ are independently O, NH, $CH_2$, CHF, CHCl, $CF_2$ or $CCl_2$;
  G is M,
  wherein:
  L is $R_1$ when both Q and T are absent; or
  L is (CO); Q is O, S, or absent; and T is $R_1$, $NHR_1$, $NR_1R_3$, $NHR_1(CO)$, a heterocyclyl or substituted heterocyclyl;
  B is a purine or an azapurine residue linked though the 9-position, as in Formula III:

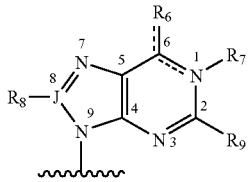

Formula III or a pyrimidine residue linked though the 1-position, as in Formula IV:

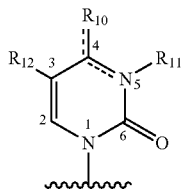

Formula IV wherein:
  $R_6$ or $R_{10}$ is hydroxy, oxo, amino, mercapto, alkylthio, alkyloxy, aryloxy, alkylamino, cycloalkylamino, aralkylamino, arylamino, diaralkylamino, diarylamino, or dialkylamino, where the alkyl groups are optionally linked to form a heterocycle; or
  $R_6$ or $R_{10}$ is acylamino, acyl(alkyl)amino, acyl(alkenyl)amino, acyl(alkynyl)amino acyl(cycloalkyl)amino, acyl(aryl)amino, acyl(aralkyl)amino, acyl(heteroaryl)amino, or acyl(heteroarylalkyl(amino); or
  $R_6$ or $R_{10}$ is di-acylamino, with the acylamino moieties optionally linked to form a heterocycle; or
  when $R_6$ in a purine or $R_{10}$ in a pyrimidine has as its first atom nitrogen, $R_6$ and $R_7$ or $R_{10}$ and $R_{11}$ are taken together to form a 5-membered fused imidazole ring, optionally substituted on the etheno ring with hydrogen, alkyl, cycloalkyl, acyl, substituted acyl, aryl, substituted aryl, aralkyl or substituted aralkyl;
  J is carbon or nitrogen, with the proviso that when J is nitrogen, $R_8$ is not present;
  $R_7$ is hydrogen, or is absent;
  $R_8$ is absent or is hydrogen, alkyl, bromo, azido, alkylamino, arylamino, aralkylamino, alkoxy, aryloxy, aralkyloxy, alkylthio, arylthio, aralkylthio, or $R_{14}(C_{1-6}\text{-alkyl})R_{13}$—;
  $R_9$ is hydrogen, chlorine, amino, monosubstituted amino, disubstituted amino, alkylthio, arylthio, or aralkylthio;
  $R_{11}$ is hydrogen or acyl;
  $R_{12}$ is hydrogen, alkyl, cycloalkyl, halo, alkenyl, substituted alkenyl, alkynyl, substituted alkynyl, aryl, substituted aryl, aralkyl or substituted aralkyl;
  $R_{13}$ is amino (—NH—), sulfide (—S—), oxo (—O—), or carbonyl; and
  $R_{14}$ is amino (—NH2), thiol (—SH), hydroxyl, or carboxyl;
  wherein the substituents of the substituted groups are independently selected from the group consisting of hydroxy, oxo, nitro, methoxy, ethoxy, alkoxy, fluoro, chloro, bromo, iodo, methyl, ethyl, propyl, butyl, alkyl, thio, thioalkyl, acyl, carboxyl, alkoxycarbonyl, carboxamido, alkylsulfonyl, alkylsulfinyl, alkylsulfonylamino, sulfonamido, cyano, amino, substituted amino, acylamino, trifluoromethyl, trifluoromethoxy, phenyl, aryl, pyridyl, imidazolyl, heteroaryl, cyclopropyl, cyclobutyl, cyclopentyl, cyclohexyl, cycloalkyl, pyrrolidinyl, piperidinyl, morpholino, and heterocyclyl.

2. The process according to claim 1, wherein said acid is a hydrogen donor and has a $pK_a$ of less than 5.

3. The process according to claim 2, wherein said acid is p-toluenesulfonic acid.

4. The process according to claim 1, wherein said solvent is aqueous tetrahydrofuran or aqueous acetonitrile.

5. The process according to claim 1, wherein B is a purine residue linked through the 9-position, as in Formula III, or a pyrimidine residue linked through the 1-position, as in Formula IV.

6. The process according to claim 1, wherein A is

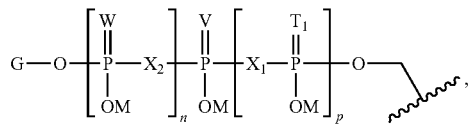

wherein n and p are 0, 1, or 2 such that the sum of n+p is from 0 to 3;
  G is M;
  $W=V=T_1=O$ or S; and
  $X_1$ and $X_2$ are independently O, NH, $CH_2$, CHF, CHCl, $CF_2$ or $CCl_2$.

7. The process according to claim 1, wherein A is T-Q-L-.

8. The process according to claim , further comprising wherein $R_6$ or $R_{10}$ is acylamino, acyl(alkyl)amino, acyl(alkenyl)amino, acyl(alkynyl)amino acyl(cycloalkyl)amino, acyl(aryl)amino, acyl(aralkyl)amino, acyl(heteroaryl)amino, or acyl(heteroarylalkyl)amino; that falls within the scope of Formula V:

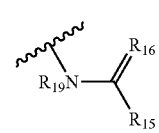

Formula V wherein:
  $NR_{19}$ is the N,N-disubstituted amino residue at the C-6 position in a purine or the N,N disubstituted amino residue at the C-4 position in a pyrimidine;
  $R_{15}$ is amino, monosubstituted amino and disubstituted amino such that the moiety according to Formula V is a urea or a thiourea;

and when present, the substituents on $R_{15}$ are alkyl, cycloalkyl, alkenyl, substituted alkenyl, alkynyl, substituted alkynyl, aralkyl, substituted aralkyl, aryl, substituted aryl, heterocyclyl and substituted hetereocyclyl; or $R_{15}$ is alkoxy, aralkyloxy, aryloxy, substituted aralkyloxy, or substituted aryloxy, such that the moiety according to Formula V is a carbamate or thiocarbamate; or $R_{15}$ is hydrogen, alkyl, cycloalkyl, alkenyl, substituted alkenyl, alkynyl, substituted alkynyl, aralkyl, substituted aralkyl, aryl, substituted aryl, heterocyclyl or substituted heterocyclyl such that the moiety according to Formula V is an amide;

$R_{16}$ is oxygen, sulfur, or NCN; and $R_{19}$ is H, alkyl, alkenyl, alkynyl, cycloalkyl, aryl, aralkyl, heteroaryl, or heteroarylalkyl; or $R_6$ or $R_{10}$ is independently di-acylamino.

9. The process according to claim 1, further comprising preparing the compound of Formula II by reacting a compound of Formula VI

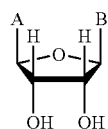

Formula VI with a compound of formula VII

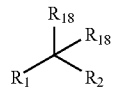

Formula VII in the presence of an organic acid, wherein $R_{18}$ is alkoxy or hydroxyl.

10. The process according to claim 9, wherein the organic acid is trifluoroacetic acid.

11. The process according to claim 9, wherein said compound of Formula VII is trans-cinnamaldehyde.

12. A process for preparing a compound of Formula XII,

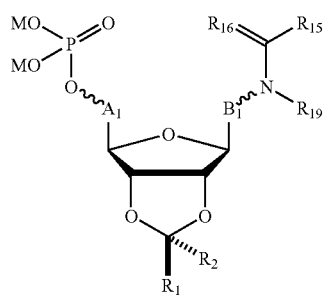

Formula XII comprising the steps of:

(a) preparing a compound of Formula I according to claim 1, wherein A is $CH_2OH$, and B is a purine or an azapurine residue as in Formula III defined by claim 1 wherine R6 is limited to the definition of R19 below;

(b) reacting the compound of Formula I with a silylating agent to form a compound of Formula IX, where $A_1$ $CH_2$, and $B_1$ is an $N^6$-substituted purinyl or an $N^4$-substituted azapurinyl residue;

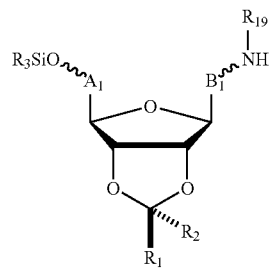

Formula IX wherein $R_{19}$ is H, alkyl, cycloalkyl, aryl, or arylalkyl, and $R_3$ is alkyl, cycloalkyl or aryl;

(c) reacting the compound of Formula IX with $R_{15}$—N=C=$R_{16}$ to form a compound of Formula X, wherein $R_{15}$ and $R_{16}$ are as defined in claim 9,

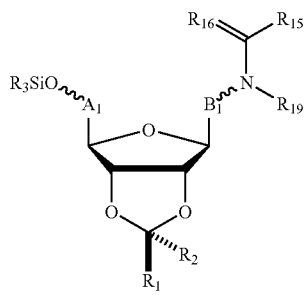

Formula X (d) reacting the compound of Formula X with a deprotecting reagent selected from the group consisting of $(R_{17})_4N^+F$, MF, and $R_{18}H^+F$ to form a compound of Formula XI;

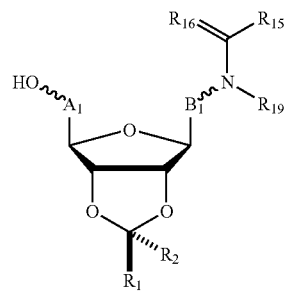

Formula XI wherein $R_{17}$ is independently H, alkyl, cycloalkyl, aryl, or heteroaryl;

M is hydrogen, $NH_4^+$, $Na^+$ or another pharmaceutically acceptable inorganic or organic counterion; and $R_{18}$ is a heteroaryl amine with at least one nitrogen in the aryl ring; and (e) reacting the compound of Formula XI with a phosphorylating agent;

whereby a compound of Formula XII is prepared.

13. The process according to claim 12, wherein $R_1$ is styryl and $R_2$ is H.

14. The process according to claim 12, wherein $R_{15}$ is ethylamino, $R_{16}$ is oxygen, and $R_{19}$ is H.

15. The process according to claim 12, wherein said deprotecting agent is a tetraalkylammonium fluoride or a trialkylhydrogenammonium fluoride, and said phosphorylating agent is phosphorous oxychloride.

16.

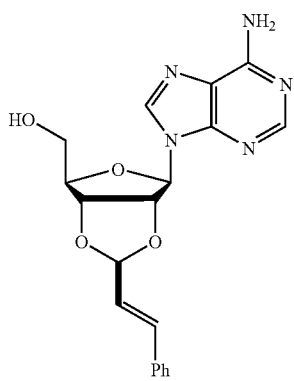

wherein Ph=phenyl.

17.

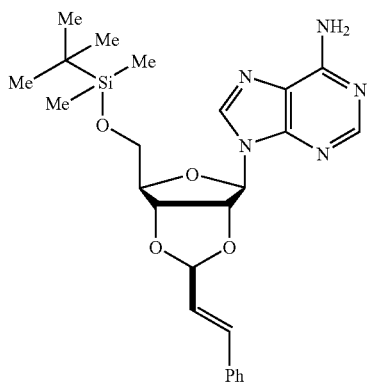

wherein Me=methyl, and Ph=phenyl.

18.

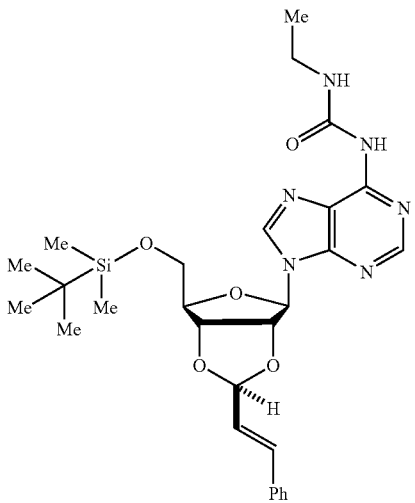

wherein Me=methyl, and Ph=phenyl.

19.

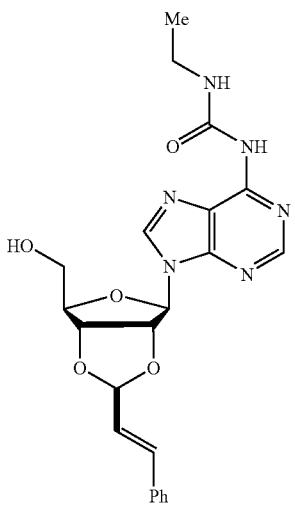

wherein Me=methyl, and Ph=phenyl.

* * * * *